(12) United States Patent
Fladoos

(10) Patent No.: US 11,540,951 B1
(45) Date of Patent: *Jan. 3, 2023

(54) FLEXIBLE ADHESIVE PHYSIO TAPE WITH THERMAL PROPERTIES

(71) Applicant: Jason Fladoos, Santa Monica, CA (US)

(72) Inventor: Jason Fladoos, Santa Monica, CA (US)

( * ) Notice: Subject to any disclaimer, the term of this patent is extended or adjusted under 35 U.S.C. 154(b) by 468 days.

This patent is subject to a terminal disclaimer.

(21) Appl. No.: 16/586,925

(22) Filed: Oct. 17, 2019

Related U.S. Application Data

(62) Division of application No. 16/022,569, filed on Jun. 28, 2018, now Pat. No. 10,492,957.

(51) Int. Cl.
*A61F 13/00* (2006.01)
*A61F 13/02* (2006.01)
*A61F 7/02* (2006.01)

(52) U.S. Cl.
CPC ........ *A61F 13/023* (2013.01); *A61F 13/0283* (2013.01); *A61F 7/02* (2013.01); *A61F 13/0246* (2013.01)

(58) Field of Classification Search
None
See application file for complete search history.

(56) References Cited

U.S. PATENT DOCUMENTS

| | | | | |
|---|---|---|---|---|
| 5,792,213 A | * | 8/1998 | Bowen | A61F 7/03 607/114 |
| 6,074,413 A | * | 6/2000 | Davis | A61F 7/03 607/108 |
| 6,096,067 A | * | 8/2000 | Cramer | A61F 7/03 607/108 |
| 6,336,935 B1 | * | 1/2002 | Davis | A61F 7/034 607/114 |
| 10,492,957 B1 | * | 12/2019 | Fladoos | A61F 13/0283 |
| 2006/0154006 A1 | * | 7/2006 | Usui | C09K 5/18 428/34.1 |
| 2008/0147153 A1 | * | 6/2008 | Quincy | A61F 7/106 607/114 |
| 2010/0241089 A1 | * | 9/2010 | Uchiyama | A61K 9/703 604/291 |
| 2017/0105877 A1 | * | 4/2017 | Buteux | B65D 75/367 |

* cited by examiner

*Primary Examiner* — Kim M Lewis
(74) *Attorney, Agent, or Firm* — William J. Benman; Benman, Brown & Williams

(57) ABSTRACT

A flexible adhesive kinesiology/physio tape adapted to produce heat from the exothermic oxidation when exposed to air. The inventive tape includes a layer of porous material with iron and salt disposed therein. In the best mode, the layer is flexible and self-adhesive. A layer of plastic is included to inhibit oxidation prior to application and use. In a preferred embodiment, the inventive flexible adhesive tape includes a first layer of flexible adhesive high quality porous fabric; a second layer of flexible adhesive high quality porous fabric; and the layer of flexible exothermic material, sandwiched between the first and second layers. The third layer can be fabricated with cellulose, iron, water, activated carbon, vermiculite and salt or fabricated with a mixture of chemical salt in dry crystal form with water. Or any other chemical mixture that creates an exothermic reaction.

4 Claims, 1 Drawing Sheet

FLEXIBLE ADHESIVE PHYSIO TAPE WITH THERMAL PROPERTIES

BACKGROUND OF THE INVENTION

Field of the Invention

The present invention relates to tapes and bindings. More specifically, the present invention relates to therapeutic physio and kinesiology tapes and bindings.

Description of the Related Art

Physio tape (aka kinesiology tape) is a tape that is used for treating athletic injuries and a variety of physical disorders. Physio tape is conventionally a thin, stretchy, elastic cotton strip with an acrylic adhesive. Therapeutic physio tape can be used to treat inflammation as well as a wide variety of musculoskeletal and sports injuries. Physio tape may be manufactured to emulate human skin in both thickness and elasticity to allow the tape to be worn without binding, constriction or restriction of movement.

Physio tapes generally provide support. However, therapists are likely to appreciate that there is a need in the art for a tape that provides support as well as thermal properties such as heat or cold.

SUMMARY OF THE INVENTION

The need in the art is addressed by the flexible adhesive kinesiology/physio tape of the present invention adapted to produce heat from the exothermic oxidation when exposed to air or appropriate catalyst. In a most general embodiment, the inventive tape includes a layer of porous material with iron and salt disposed therein. In the best mode, the layer is flexible and self-adhesive. A layer of plastic is included to inhibit oxidation prior to application and use.

In a preferred embodiment, the inventive flexible adhesive kinesiology or physio tape with thermal heating properties includes a first layer of flexible adhesive high quality porous fabric; a second layer of flexible adhesive high quality porous fabric; and the layer of flexible exothermic material, sandwiched between the first and second layers. The third layer can be fabricated with cellulose, iron, water, activated carbon, vermiculite and salt.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
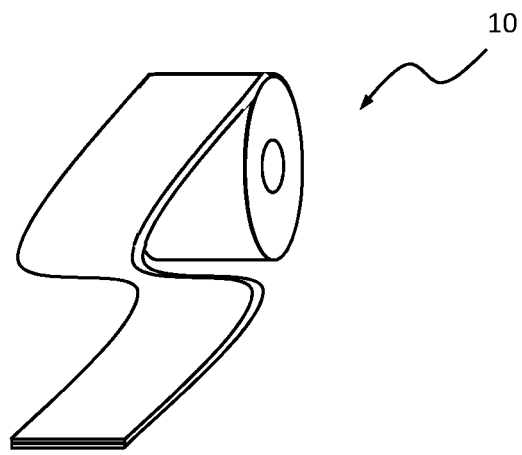
FIG. 1 is a perspective view of a roll of thermal tape implemented in accordance with the teachings of the present invention.

FIG. 1 is a perspective view of a roll of thermal tape implemented in accordance with the teachings of the present invention.

Figure 2:
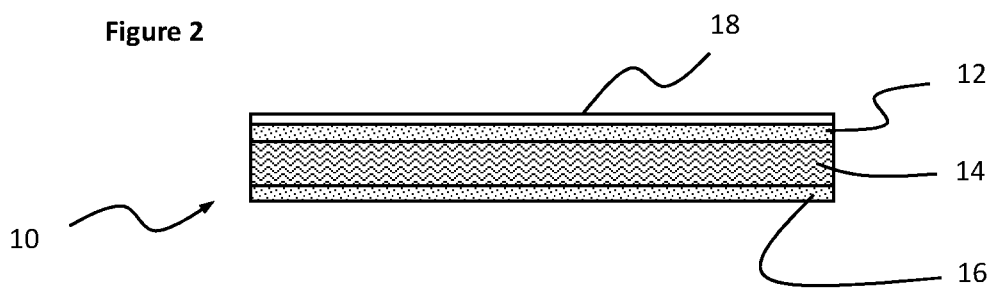
FIG. 2 is a sectional end view of the tape depicted in FIG. 1.

FIG. 2 is a sectional end view of the tape depicted in FIG. 1. As shown in FIGS. 1 and 2, the present invention is flexible adhesive kinesiology/physio tape adapted to produce heat from the exothermic oxidation when exposed to air. In the preferred embodiment, the inventive flexible adhesive kinesiology or physio tape 10 with thermal heating properties includes a first layer 12 of flexible adhesive high quality porous fabric, a second layer 16 of flexible self-adhesive or skin-adhesive high quality porous fabric; and a layer 14 of flexible exothermic material, sandwiched between the first and second layers 12 and 16 respectively. The third layer 14 can be fabricated with cellulose, iron, water, activated carbon, vermiculite and salt. Layer 14 can be created as a layer saturated or interwoven with the reactants or it can be implemented as a powder in a channel with sealed edges and ends. A layer 18 of plastic, or other suitable material, is included to inhibit oxidation prior to application and use.

The inventive tape 10 may be fabricated by applying a strong adhesive such as zinc oxide or other suitable adhesive to a large sheet of high quality porous fabric 16 such as a blend of cotton, latex and/or nylon.

Next, to create the exothermic layer 14, cellulose, iron, water, activated carbon, vermiculite and salt are mixed in a vacuum and in a manner used in the fabrication of conventional hand warmers and applied to the fabric. See, for example, U.S. Pat. No. 6,096,067, entitled DISPOSABLE THERMAL BODY PAD, issued Aug. 1, 2000, to Cramer et al. the teachings of which are hereby incorporated herein by reference.

Next, the top layer 12, fabricated in the same manner as the bottom layer 16, is applied to the exothermic layer 14. The top and bottom layers 12 and 16 may be 97% tightly woven elasticated cotton with 3% nylon fibers or implemented with a ratio of cotton or nylon better suited for a particular application.

Finally, the top plastic layer 18 is applied to top layer 12 to prevent oxidation prior to use. The sheet is then rolled and cut.

In the best mode, the tape has a width of 1-4 inches, a thickness of 1-5 cm and a length of 6 inches to any length. The tape can be manufactured to have segmented lengths of exothermic reactants to allow for the tape to be cut at various lengths without cutting through the pouch of reactants.

In an alternative embodiment, a hollow section of the tape 10 could be provided and filled with a pre-made, plastic, enclosed tube of reactants. This eliminates the need for the tape to be leak proof. This also simplifies the manufacturing process as the tape can be made with a hollow core and then tubes can be inserted that are either filled with reactants that cool or heat. Those tubes can also be filled with varying quantities depending on the desired intensity of heat or cool.

Those of ordinary skill in the art will appreciate that the present invention is not limited to the fabrics and chemicals disclosed herein. Other combinations of fabrics and chemicals may be employed without departing from the scope of the present teachings. For example, a plurality of small capsules may be provided within the tape which, when squeezed by a user, ruptures and releases a mix of chemicals leading to an enthalpy heating effect.

In another implementation, the capsules may be filled with a supersaturated solution of sodium acetate in water. In this case, crystallization is triggered by flexing a small flat disc of notched ferrous metal embedded in the liquid. Pressing the disc releases very tiny adhered crystals of sodium acetate into the solution which then act as nucleation sites for the crystallization of the sodium acetate into the hydrated salt (sodium acetate trihydrate, $CH_3COONa.3H_2O$). Because the liquid is supersaturated, this makes the solution crystallize suddenly, thereby releasing the energy of the crystal lattice.

In a multi-use/reusable embodiment of the present teachings, heat is produced by mixing a chemical salt in dry crystal form with water. By way of example, suitable dry chemical salt examples include calcium chloride, magnesium sulfate and sodium acetate however the invention is not limited thereto. The solution is super saturated meaning it has been heated to dissolve more salt. When an internal metal strip (usually stainless steel) is bent, tiny particles of metal are released which offer nucleation sites causing crystals to form releasing the stored heat energy of the solution.

There are multiple ways to vary the intensity and/or duration of the heating/cooling. For example, changing the concentration and/or quantity of the reactants would control the duration of hot/cold and also the intensity. This allows for multiple choices of the thermal tape depending on the environment and length of time heating or cooling is desired.

Multiple Isolated Channels

In order to vary the intensity and/or duration of the chemical heating, one can have multiple, side by side, isolated channels of reactants going the length of the tape. Simultaneous activation of multiple channels could provide more intense heat. Sequential activation of the channels could allow for longer duration of heat as you can activate the next channel once the previous has diminished. One could also have separate hot or cold channels containing different reactants so one piece of tape could provide both hot and cold. In addition, separate plastic strips could be included to release more heat later.

Chemical heat could be produced via a chemical reaction induced by mechanical activation or via a triggered temperature or biomechanical sensor.

Those having ordinary skill in the art and access to the present teachings will recognize additional modifications, applications and embodiments within the scope thereof.

It is therefore intended by the appended claims to cover any and all such applications, modifications and embodiments within the scope of the present invention.

The invention claimed is:

1. A flexible adhesive kinesiology or physio tape with thermal heating properties including:
   a first elastic layer of flexible material;
   a second elastic layer of flexible material; and
   a third elastic layer, sandwiched between said first and second layers, of flexible exothermic material.

2. The flexible adhesive kinesiology or physio tape with thermal heating properties of claim 1 wherein said third layer produces heat from an exothermic oxidation when exposed to air.

3. The flexible adhesive kinesiology or physio tape with thermal heating properties of claim 2 wherein said third layer includes cellulose, iron, water, activated carbon, vermiculite and salt.

4. The flexible adhesive kinesiology or physio tape with thermal heating properties of claim 1 wherein said first or said second layer includes adhesive.

\* \* \* \* \*